United States Patent [19]

Peters

[11] Patent Number: 5,160,314
[45] Date of Patent: Nov. 3, 1992

[54] WRIST SUPPORT

[75] Inventor: Helena Peters, Bromma, Sweden

[73] Assignees: Bissell Healthcare Co.; Camp International, Inc., both of Jackson, Mich.

[21] Appl. No.: 692,166

[22] Filed: Apr. 26, 1991

[51] Int. Cl.$^5$ ............................................. A61F 5/10
[52] U.S. Cl. ........................................ 602/21; 602/64
[58] Field of Search ..................... 128/77, 26, 87 R; 602/5, 21, 62-64; 273/54 B

[56] References Cited

U.S. PATENT DOCUMENTS

| | | |
|---|---|---|
| D. 259,955 | 7/1981 | Helferich . |
| 4,013,070 | 3/1977 | Harroff . |
| 4,084,586 | 4/1978 | Hettick . |
| 4,138,108 | 2/1979 | Robinson ........................... 273/54 B |
| 4,183,098 | 1/1980 | Knowles, Jr. . |
| 4,228,548 | 10/1980 | Cohen ................. 273/54 B X |
| 4,309,991 | 1/1982 | DeMarco ............... 273/54 B X |
| 4,807,609 | 2/1989 | Meals . |
| 4,854,309 | 8/1989 | Elsey . |
| 4,862,877 | 9/1989 | Barber . |
| 4,915,097 | 4/1990 | West . |
| 5,014,689 | 5/1991 | Meunchen . |

*Primary Examiner*—Richard J. Apley
*Assistant Examiner*—Linda C. M. Dvorak
*Attorney, Agent, or Firm*—Price, Heneveld, Cooper, DeWitt & Litton

[57] ABSTRACT

A unitary body support adapted to be pulled onto and positioned about the hand and wrist area and adapted to anatomically conform to the wrist and basal hand of the wearer comprises a sleeve constructed of a resilient elasticized fabric including an outer layer having a brushed looped texture. The sleeve is provided with a thumb opening and means for receiving a palmar stabilizing stay, with the stay being removable. The sleeve includes an integral compression strap which is sufficiently long to extend around the wrist at least once and which is provided at its free end with hook attachment means for releasable engagement with the outer fabric loops. The sleeve also includes means which makes pulling the sleeve on easier and for adjusting the wrist opening to accommodate to the wrist girth.

14 Claims, 2 Drawing Sheets

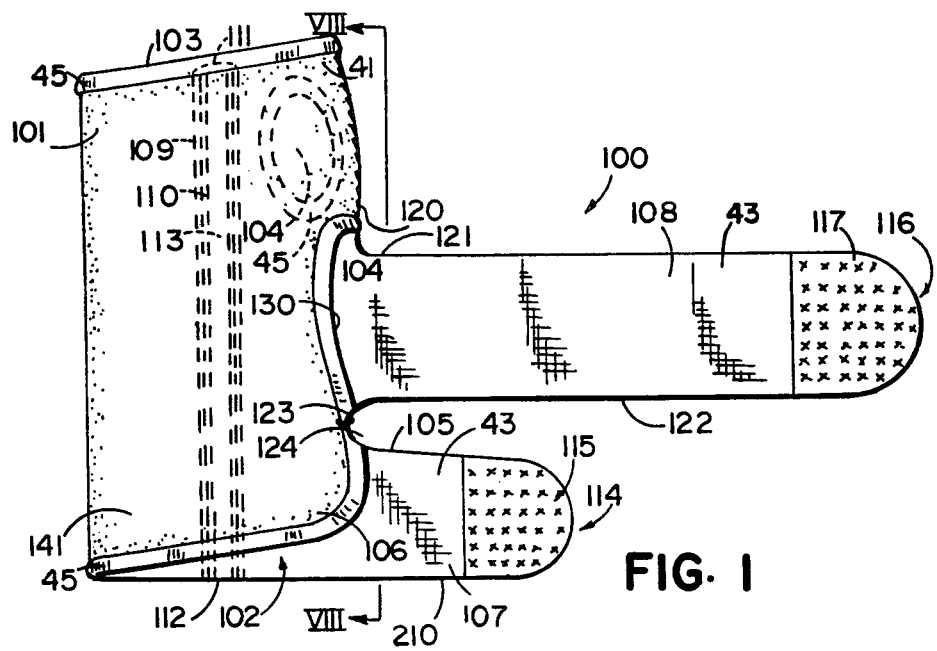
FIG. 1
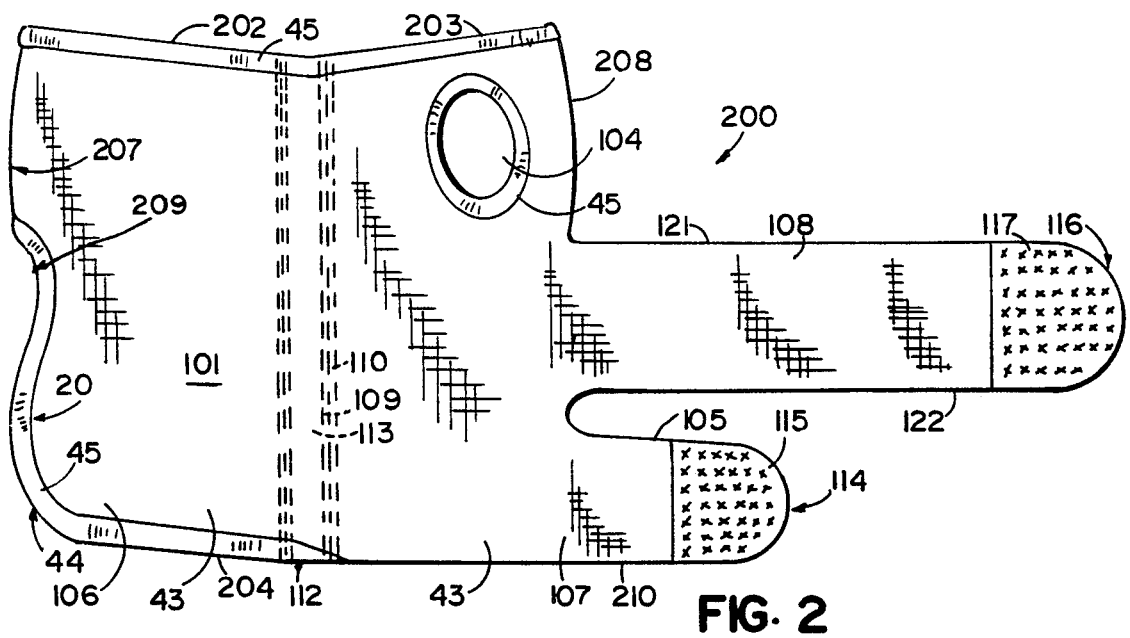
FIG. 2
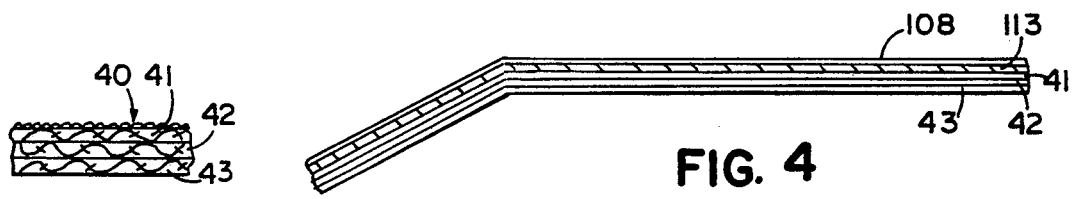
FIG. 3
FIG. 4

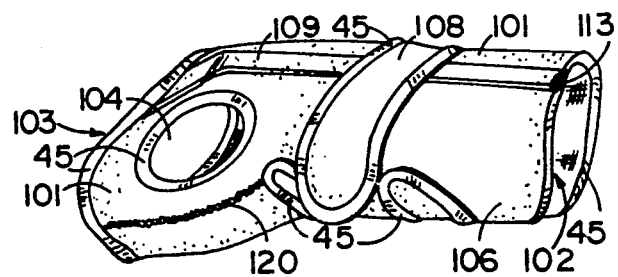
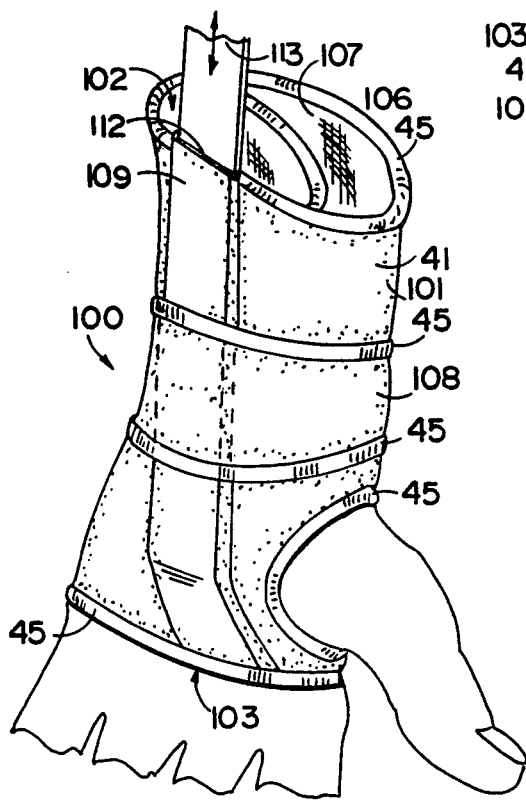
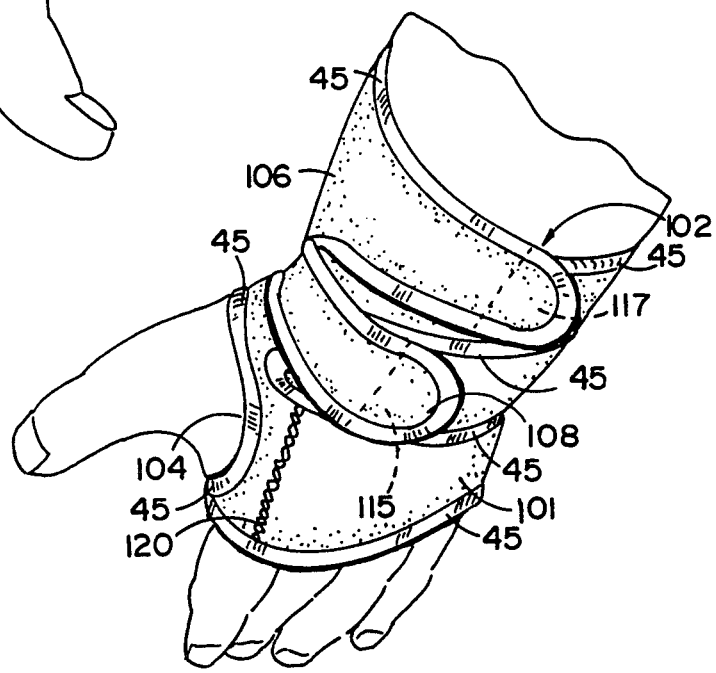
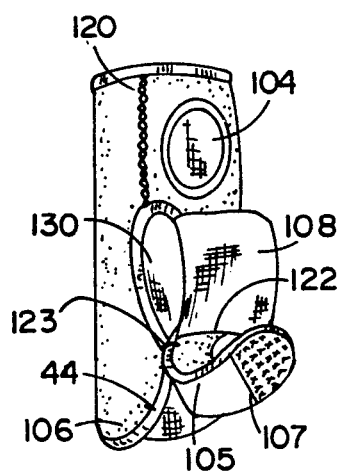

WRIST SUPPORT

BACKGROUND OF THE INVENTION

This invention relates to an orthotic device comprising a one-piece support for providing pain relief and stabilization in the carpal area.

Numerous elastic and inelastic therapeutic devices have been developed which can be placed about the wrist area in order to relieve the pain and trauma associated with injuries and diseases to the wrist, as well as to simply provide support for weakened wrists. Wrist supports should provide compression and/or stabilization of the wrist and/or should position and maintain the hand in a cock-up position. With many, there is difficulty in regulating the degree of compression. If too tight, the support may affect circulation to the injured or weak area. Others simply have no means for adjusting compression. In many instances, the devices do not stay in place in the wrist area. Other approaches, such as using adhesive tape and elastic band members such as the well-known "Ace" bandage, require considerable expertise to ensure that the wrist is properly wrapped for correct support while, at the same time, not limiting circulation to and from the member.

Desirable features for wrist supports, particularly those which are intended to provide relief from problems such as carpal tunnel syndrome, tendonitis, arthritis, wrist strains or sprains, post-wrist fractures and the like and preferably are easily put on and removed by the user. In many of the prior art devices, it is extremely difficult, if not impossible, for the individual to properly install the wrist support without help. Other desirable features include lightweight, washability and durability. One of the more important considerations to the wearer is a combination of comfort and at least partial use of the hand during wear. Comfort requires soft edges and surfaces to prevent pressure problems and irritation to the affected area as well as enough exposure to the atmosphere to minimize perspiration. The wrist support must take into consideration the normal palmar arch of the hand and the ball of the thumb should be kept free, if possible, to permit movement of the thumb during wearing of the support and the palmar support, if provided, should be proximal to the palmar crease to allow full use of the fingers.

SUMMARY OF THE INVENTION

The orthotic device of the present invention comprises a ready-to-wear one-piece pull-on wrist support adapted to anatomically conform to the shape of the wrist at the carpal area, including the lower or distal forearm and the proximal palm area to the palmar crease. The support is formed from a resilient flexible unitary sheath adapted to conform to the body member.

The sheath includes a forearm opening, a palmar opening and a thumb opening therebetween. The support includes an adjustable closure means at its forearm opening end and an integral compression strap located between the forearm opening and the thumb opening. The compression strap is sufficiently long to extend around the wrist at least once just above the hand.

BRIEF DESCRIPTION OF THE DRAWINGS

FIG. 1 is a rear elevational view of the wrist support of the invention with the compression strap extended in unwrapped position;

FIG. 2 is a planar view of the wrist support of the invention prior to forming the support;

FIG. 3 is a partial cross-sectional view of the resilient fabric laminate;

FIG. 4 is a partial cross-sectional view taken through the palmar support;

FIG. 5 is a perspective view of the wrist support;

FIG. 6 is a perspective view of the wrist support and demonstrating the removable feature of the palmar support;

FIG. 7 is a perspective view of the wrist support in place on the left hand of the wearer; and FIG. 8 is a cross-sectional view taken along the plane VIII—VIII of FIG. 1.

DESCRIPTION OF THE PREFERRED EMBODIMENTS

In the preferred embodiments, at least a portion of the exposed outer surface 41 comprises a brushed texture having looped fastening means. The compression strap 108 is provided at its free end 116 on its inner surface 43 with a pad 117 comprising hooked fastening means for cooperative releasable engagement with the looped fastening means of the outer surface. The support 100 also includes a pocket 110 which is sewn to the outside surface 41 for removably receiving a manually bendable support medium 113 having a substantially rectangular shape. The support medium 113 substantially conforms to the palm area and positions the hand in what is referred to as a "cock-up" position. It can be shaped to increase or decrease the degree of elevation of the "cock-up" position. It approximately extends the length of the wrist support. This support is especially useful for those having carpal tunnel syndrome. The support medium 113 may or may not be used, depending on the type of support desired. The compression strap 108 is wrapped over the support 100 and about the wrist at least once and the hook fastening pad 117 at the free end 116 of the wrap strip 108 on its inner side 43 is affixed to the looped fastening means of the outer surface 41. An adjustable closure means is located at the forearm opening end of the support and includes a forearm closure tab 106 having a free end for adjustment to accommodate size variances of the wrist area and an integral wrist closure strap 107 which has a hooked closure means 115 at its free end 114 for attachment to the outer surface 41 of the support.

The wrist support of the invention is formed from a resilient flexible material comprising an exposed outer surface or layer and an inner layer or surface adapted to be worn next to the body area. More particularly, the supports of this invention can be formed from substantially any natural or synthetic material, including both inelastic and elastic materials, having sufficient flexibility and resiliency to enable the support to anatomically conform to the body member to which it is applied. In addition, the supports include mutually intercooperating connector means comprising loop keeper means on at least a portion of the outer surface of the support and a companionate array of hook keeper means on at least a portion of the inner surface of the support which confront the loop keeper means when both keeper means are in an overlying relationship on the supports; the hook means being adapted in response to pressure against the loop means to intermesh with the loop means and releasably cling to the loop means, to be separated therefrom in response to a peeling quick yanking force.

The resilient flexible natural or synthetic materials suitable for use in the practice of the invention include fabrics made from inelastic fibers such as nylon fibers, polyester fibers, cotton fibers and the like; elastomers such as natural rubber, neoprene rubber and the like; and elasticized fibers comprising a blend of at least one inelastic fiber, such as nylon, polyester, cotton and the like and at least one elastomeric fiber, such as those sold under the trademark Lycra, and including combinations of two or more natural and/or synthetic materials, generally in the form of a laminated structure.

The preferred material comprises a flexible resilient elasticized fabric laminate comprising an outer elasticized fabric layer, an open-cell polymeric foam core and an inner or proximal elasticized fabric layer. The foam core is coextensive with and adhered to both inner and outer layers. The laminate is stretchable in all directions. The inner and outer layers comprise elasticized fabrics having substantially the same degree of stretch in all directions. The outer elasticized fabric layer is preferably a high moisture absorbent fabric comprising a blend of at least one inelastic fiber and at least one elastic fiber, with a blend of inelastic polyamide and elastic polyurethane being currently preferred. The outer surface has a brushed felt-like texture comprising myriad upstanding and relatively free fiber loop fastening means. The inner layer is preferably a lower moisture absorbent but good wicking fabric comprising an elasticized cotton fabric comprising a blend of cotton and at least one elastic fiber, preferably an elastic polyurethane fiber. The polymeric foam core is an open-celled cellular material which is preferably a polyurethane or polystyrene foam and is most preferably a polyethylene foam. Currently, a preferred composite comprises 35 weight percent polyamide, 42 weight percent cotton, 18 weight percent polyurethane elastic fiber and 5 weight percent open-cell polyethylene foam, based on total weight of the composite. The provision of elasticized fibers and fabrics from different natural and synthetic fibers is well-known in the art, and there is no need for elaboration. The composite is lightweight, stretchable to anatomically conform to the body member, durable and easily laundered in home washing machines. Drip-drying is the preferred method of drying laundered supports. The high-absorbent elasticized outer layer, the open-cell polymeric foam core and the low-absorbent elasticized inner layer cooperatively provide a breathable composite which aids in the transfer of moisture, such as perspiration from the wearer's body to the outer surface of the outer or exposed layer, which has sufficient porosity to enable moisture to be wicked from the body to the outer surface of the support. The elasticized cotton inner layer ensures dryness, provides a comfortable feel against the body and a feeling of soothing warmth for injured and arthritic joints when engaging in strenuous activities while minimizing heat buildup during such activities.

Referring now to the drawings, the wrist support 100 of the invention comprises a substantially curvilinear resilient sheath 101 having a forearm opening 102; a hand opening 103 and a thumb opening 104. The forearm opening 102 is adjustable by means of the edge portions 105 and 106 defined by forearm closure tab 106 and wrist closure strap 107 to accommodate to variations in girth of the forearm area. Edges 105 and 106 converge toward each other (FIG. 8) and are attached at the short seam 123. Support 100 also includes an integral elongated compression wrap strap 108 and a palmar reinforcing strip 109 fixedly attached, as by sewing, to outer surface 41. Reinforcing strip 109 and outer surface 41 together define a pocket 110 having a closed bottom 111 and an open top 112 for receiving palmar stay 113. Closure strap 107 includes on its inner surface 43 and at its free end 114 a fastening means 115 preferably comprising hooked fastening means for releasable attachment to outer surface 41, which preferably has a brushed texture comprising looped fastening means.

Compression strap 108 includes on its inner surface 43, at its free end 116, fastening means 117, preferably comprising hooked fastening means for releasable attachment to outer surface 41. Compression strap 108 is of sufficient length to extend around the wrist and across palmar reinforcing strip 109 at least once and secured on the dorsal side of the support 100. Palmar stay 113 comprises an elongated rectangular shaped rigid material which is rigid but deformable, such as an elongated rectangular metal strip, for conforming to the proximal palmar area.

Support 100 also includes a seam 120 extending from hand opening 103 to an opening 130 where it merges into side 121 of compression strap 108 that extends from the side of opening 130. Compression strap 108 and forearm closure strap 107 are substantially parallel. Edge 122 of compression strap 108, edge 123 of closure strap 107 and edge 105 merge at point 123 where they are attached to each other by a short stitch (FIGS. 1 and 8). The stitch at point 123 provides a merging intersection of free tab 106 and the basal portion of closure wrap 107 (FIG. 8) to provide for an enlarged forearm opening in the sidewall of sheath 101 and also stabilizes the side wall of sheath 101 adjacent forearm opening 102. Exposed edges of support 100 are covered by elastic binding 45.

As disclosed in FIG. 3, support 100 is formed from an elasticized fabric laminate comprising a moisture absorbent elasticized fabric outer surface 41 and a low moisture absorbent elasticized inner surface 43 which is the skin side of the laminate. The laminate also includes a thin (0.1–0.3 inch) open-cell polymeric foam core is bonded to both the outer and inner surfaces and is coextensive with each. The outer fabric has a loop type outer surface and comprises a blend of at least one inelastic fiber and at least one elastomeric fiber, with a polyamide elastomeric polyurethane blend being currently preferred. The inner fabric comprises a blend of cotton fiber and at least one elastomeric fiber, with an elastomeric polyurethane being the current elastomeric fiber of choice. Substantially any polymeric foam can be used for the core material, with open-cell polyurethane, polystyrene and polyethylene being preferred. An open-cell polyethylene foam is the current core material of choice. A particularly preferred construction comprises 35 weight percent polyamide fiber, 42 weight percent cotton fiber, 18 weight percent polyurethane elastomeric fiber and 5 weight percent polyethylene open-cell foam, based on total weight of the fabric laminate. The elasticized fabric laminate is stretchable in all directions. The elasticity or stretchability of the outer surface 41 and the inner surface 43 is substantially the same. When formed into support 100, all exposed edges of fabric laminate 40 are covered by elasticized binding 44 (not shown in FIG. 3).

The construction of wrist support 100 is further illustrated in FIG. 2, which shows a die-cut pattern 200 from which wrist support 100 is sewn. As shown in FIG. 1, pattern 200 comprises an irregularly shaped main body 101 having inner side 43 appearing to the viewer. Main body 101 comprises edges 202 and 203 of substantially equal length. Each edge slopes inwardly at the same angle of slope to the point of their intersection to form a shallow concave surface defining the palmar end of support 100. At one side region, main body 101 is provided with a flat concave edge 207 depending from an end of edge 202. It merges into edge 209 which is tangentially radiused into edge 204, which defines the wrist end of support 100. Edge 209 has an arcuate shape for forming the opening 130. At the opposite end region, main body 101 includes a shallow convex edge 208 depending from an end of edge 203. Concave edge 207 and convex edge 208 are of substantially the same length and the curvature of each edge is such that the two edges will mate together to form a line joint. Edge 208 is tangentially radiused into edge 121 of integral wrist compression strap 108. Integral strap 108 extends outwardly from main body 101 and comprises parallel edges 121 and 122. The length of strap 108 is sufficient to completely encircle support 100 at least once. In the embodiment shown, edges 121 and 122 are radiusly merged into each other to form free end 116. Edges 121 and 122 are radiusly merged at the base of strap 108 into main body 101. This opposite end region also includes integral forearm closure strap 107, which extends outwardly from main body 101 and which comprises parallel edges 105 and 210. The length of strap 107 is preferably of sufficient length so that when in place on a wrist it extends across at least the middle region of the dorsal side of the lower forearm. In the embodiment shown, edges 105 and 210 are radiusly merged into each other to form free end 114. It will be appreciated that free ends 114 and 116, of straps 107 and 108, respectively, may have other geometrical designs than that shown in the disclosed embodiment. Edge 105 is radiusly merged at the base of strap 107 into main body 101. The merging of edge 105 of strap 107 and edge 122 of strap 108 into main body 101 defines a U-shaped recess 124. The opposite parallel edge 210 of strap 107 merges at the base of strap 107 into edge 204 of main body 101 to complete the definition of the wrist end of support 100. Main body 101 is also provided with thumb opening 104 which is located within the interior angle formed by the intersection of edges 203 and 208, just above (in the shown view) an imaginary extension of edge 121.

To form support 100 from the cutout material of pattern 200, edges 207 and 208 are mated together and the resulting line joint is stitched to form seam 120. Reinforcing strip 108 is positioned on the palmar side of support 100 on outer surface 41 at the approximate midpoint of the palmar side to extend vertically between the palmar and wrist ends, by vertically sewing each side to define pocket 109. All exposed edges are covered with elastic binding 45 which is stitched around the periphery of the edges. The binding covers the palmar end of reinforcing strip 109, secures strip 108 at the bottom side and forms the closed end 111 of pocket 109. The outside edges of the reinforcing strip are stitched vertically to fabric surface 41 to complete pocket 109 with the pocket having an open end 112 at the wrist end for inserting and removing metal palmar stabilizing stay 113. The hook fastening pads 115 and 117 are fixedly attached to free ends 114 and 116 of straps 107 and 108, respectively, on the inner fabric surface 43 of each strap. The adjustable part of forearm opening 102 is formed by joining, as by sewing, edges 122, 105 and 44 at the point 123 permitting tab 106 and strap 107 to be separated to open the opening 102. As previously disclosed, above the stitch at point 123, the opening 130 is formed by reason of the arcuate shape of edge 209 which is not stitched to strap 108 which extends from one side of opening 130 (FIGS. 1 and 8).

As shown in FIGS. 1, 2 and 4, palmar stabilizing stay 113 comprises a unitary elongated generally rectangular rigid material, preferably aluminum, which is rigid but bendable to conform substantially to the contour of the hand, between the basal or wrist end and the palmar crease. It will typically be pre-bent, but can be re-bent by the user, if desired, for better conformance. The palmar stay 113 can be removed whenever desired, as shown in FIG. 6.

The wrist support is easily put on by the wearer, without required aid from another person. In the embodiment shown (FIGS. 4 and 5), the left hand is inserted into the wrist opening with the palmar side disposed towards the palm. The sheath 101 is drawn over the hand and wrist, with the thumb being inserted into the thumb opening 104. The drawing of the sheath over the hand is greatly simplified by the enlarged opening 102 permitted by the separation of tab 106 and strap 107 and also the opening 130 which minimizes the obstruction to the hand. After the wrist is in place, the compression strap 108 is drawn around the wrist at least once, with an amount of tension sufficient to draw the palmar stay 112 into close conformance with the underside of the wrist area and provide the desired degree of compression, which is distributed substantially uniformly to the injured or weakened wrist, and which will improve stabilization of the wrist area and prevent movement of the support. Although shown and described for the left wrist, it will be readily apparent that reversal of pattern 200 will provide a wrist support adapted for use on the right wrist. The protrusion of the thumb through the thumb opening leaves the thumb free to move, and the extremities of the hand below the palmar crease are also free to move in a substantially normal manner.

The wrist support 100, with the thumb protruding from the thumb opening 104, will properly locate the wrist support with the palmar reinforcing strip 109 (which may include a palmar stay 113) located across the middle region of the hand. Once properly located, the encircling strap 108 is pulled with an amount of tension sufficient to provide a desired degree of compression which will force the palmar reinforcing stay 113 or support 100 to conform more closely to the wrist contour. The strap 108 is wrapped around the wrist at least once and secured to the outer surface 41 of the fabric by its hook tab means 117. Tension is then applied to the closure tab 106 to conform the circumference of the wrap to the girth of the wrist area and the wrist closure leg 107 is pulled across the tab 106 and affixed to the outer surface 41.

The encircling strap 108 extends over the palmar stay 113 completely around the support 100 at least once, and adjustable effective compression and firm stabilization of the stay is achieved to provide the required stability and prevent the support 100 from shifting its position. It will be appreciated that compression may be adjusted to a desired level by increasing or decreasing the tightness of the encircling strap 108.

While a single embodiment of this invention has been disclosed with particularity above, numerous modifications of the same within the scope of the invention will be readily apparent to those skilled in the art. Thus, it is considered that various configurational modification of the wrist support of this invention will occur to those skilled in the art and are considered also to be encompassed by this invention. Further, the scope of the invention of this support, which is suitable for the treatment and prevention of injuries to the wrist area, is to be limited solely by the claims appended hereto.

The embodiments of the invention in which an exclusive property or privilege is claimed are defined as follows.

1. A pull-on wrist support adapted to be pulled onto the hand and wrist and to anatomically conform to the body in the hand and wrist area comprising:

a sheet of resilient, elastic fabric material shaped to define (1) a main body with top, bottom and opposed side edges, and an inner and an outer surface, and (2) an integral elongated compression strap integral with and extending from said main body approximately midway along one of said side edges such that a portion of said side edge extends above and a portion of said side edge extends below said compression strap;

said side edges being seamed together with said inner surface of said main body facing inwardly and said outer surface facing outwardly, said seam extending at least from approximately said bottom edge of said main body to said elongated compression strap, but said side edges being separated at least from approximately the top of said compression strap, to thereby define a sleeve portion with a bottom opening and a top opening through which a user's hand extends;

a thumb opening in said sleeve portion;

closure means located above said compression strap for bringing said separated side edges together above said elongated compression strap to thereby close said main body upon itself and define an upper opening in said wrist support through which a user's forearm extends;

said compression strap and said outer surface of said main body including cooperating releasable attachment means, and said strap extending from said main body in a direction such that, and having a sufficient length such that, said compression strap encircles the wrist area at least once in use, whereby after a user's hand and wrist have been inserted into said wrist support, said compression strap can be wrapped snugly around the wrist and releasably fastened to said outer surface of said main body.

2. The wrist support of claim 1 in which said closure means is releasable such that said support can be opened up to facilitate ease of application.

3. A pull-on wrist support adapted to be pulled onto the hand and wrist and to anatomically conform to the body in the hand and wrist area comprising:

a sheet of resilient, elastic fabric material shaped to define (1) a main body with top, bottom and opposed side edges, and an inner and an outer surface, and (2) an integral elongated compression strap integral with and extending from said main body approximately midway along one of said side edges such that a portion of said side edge extends above and a portion of said side edge extends below said compression strap;

said side edges being seamed together with said inner surface of said main body facing inwardly and said outer surface facing outwardly, said seam extending at least from approximately said bottom edge of said main body to said elongated compression strap, to thereby define a sleeve portion with a bottom opening and a top opening through which a user's hand extends;

a thumb opening in said sleeve portion;

said compression strap and said outer surface of said main body including cooperating releasable attachment means, and said strap extending from said main body in a direction such that, and having a sufficient length such that, said compression strap encircles the wrist area at least once in use, whereby after a user's hand and wrist have been inserted into said wrist support, said compression strap can be wrapped snugly around the wrist and releasably fastened to said outer surface of said main body;

a closure strap integrally formed of said sheet of resilient, elastic fabric and extending from said main body along said one edge thereof, separate from and above said compression strap and generally adjacent said top edge of said main body;

said closure strap and said outer surface of said main body including cooperating releasable attachment means whereby said main body can be opened or can be closed upon itself to define an upper opening in said wrist support through which a user's forearm extends.

4. The wrist support of claim 3 in which said cooperating releasable attachment means associated with said closure strap facilitate adjustment of the attachment of said closure strap to said outer surface such that the diameter of said wrist support at said closure strap can be adjusted.

5. The wrist support of claim 4 in which said cooperating releasable attachment means associated with said compression strap and said outer surface of said main body facilitate adjustable releasable attachment of said compression strap such that the compression on the user's wrist can be adjusted.

6. The wrist support of claim 5 in which said splint includes palmar stabilizing means secured to said main body in a position relative to said thumb opening such that said stabilizing means extends along the user's palm.

7. The wrist support of claim 6 in which said side edges are also seamed together at a point lying between said compression strap and said closure strap.

8. The wrist support of claim 2 in which said closure means is releasably adjustable such that the diameter of said splint at said closure means can be adjusted.

9. The wrist support of claim 8 in which said wrist support includes palmar stabilizing means secured to said main body in a position relative to said thumb opening such that said stabilizing means extends along the user's palm.

10. A pull-on wrist support adapted to be pulled onto the hand and wrist and to anatomically conform to the body in the hand and wrist area comprising:

a sheet of resilient, elastic fabric material shaped to define (1) a main body with top, bottom and opposed side edges, and an inner and an outer surface, and (2) an integral elongated compression strap integral with and extending from said main body approximately midway along one of said side edges such that a portion of said side edge extends above and a portion of said side edge extends below said compression strap;

said side edges being seamed together with said inner surface of said main body facing inwardly and said outer surface facing outwardly, said seam extending at least from approximately said bottom edge of said main body to said elongated compression strap, to thereby define a sleeve portion with a bottom opening and a top opening through which a user's hand extends;

a thumb opening in said sleeve portion;

closure means for bringing said side edges together above said elongated compression strap to thereby close said main body itself and define an upper opening in said wrist support through which a user's forearm extends;

said compression strap and said outer surface of said main body including cooperating releasable attachment means, and said strap extending from said main body in a direction such that, and having a sufficient length such that, said compression strap encircles the wrist area at least once in use, whereby after a user's hand and wrist have been inserted into said wrist support, said compression strap can be wrapped snugly around the wrist and releasably fastened to said outer surface of said main body;

said closure means being releasable such that said support can be opened up to facilitate ease of application;

said closure means being releasably adjustable such that the diameter of said splint at said closure strap can be adjusted;

said wrist support including palmar stabilizing means secured to said main body in a position relative to said thumb opening such that said stabilizing means extends along the user's palm;

said side edges also being seamed together at a point lying between said compression strap and said closure means.

11. The wrist support of claim 1 in which said cooperating releasable attachment means associated with said compression strap and said outer surface of said main body facilitate adjustable releasable attachment of said compression strap such that the compression on the user's wrist can be adjusted.

12. The wrist support of claim 11 in which said wrist support includes palmar stabilizing means secured to said main body in a position relative to said thumb opening such that said stabilizing means extends along the user's palm.

13. A pull-on wrist support adapted to be pulled onto the hand and wrist and to anatomically conform to the body in the hand and wrist area comprising:

a sheet of resilient, elastic fabric material shaped to define (1) a main body with top, bottom and opposed side edges, and an inner end and an outer surface, and (2) an integral elongated compression strap integral with and extending from said main body approximately midway along one of said side edges such that a portion of said side edge extends above and a portion of said side edge extends below said compression strap;

said side edges being seamed together with said inner surface of said main body facing inwardly and said outer surface facing outwardly, said seam extending at least from approximately said bottom edge of said main body to said elongated compression strap, to thereby define a sleeve portion with a bottom opening and a top opening through which a user's hand extends;

a thumb opening in said sleeve portion;

closure means for bringing said side edges together above said elongated compression strap to thereby close said main body upon itself and define an upper opening in said wrist support through which a user's forearm extends;

said compression strap and said outer surface of said main body including cooperating releasable attachment means, and said strap extending from said main body in a direction such that, and having a sufficient length such that, said compression strap encircles the wrist area at least once in use, whereby after a user's hand and wrist have been inserted into said wrist support, said compression strap can be wrapped snugly around the wrist and releasably fastened to said outer surface of said main body;

said cooperating releasable attachment means associated with said compression strap and said outer surface of said main body facilitate adjustable releasable attachment of said compression strap such that the compression on the user's wrist can be adjusted;

said wrist support including palmar stabilizing means secured to said main body in a position relative to said thumb opening such that said stabilizing means extends along the user's palm;

said side edges also being seamed together at a point lying between said compression strap and said closure means.

14. A pull-on wrist support adapted to be pulled onto the hand and wrist and to anatomically conform to the body in the hand and wrist area comprising:

a sheet of resilient, elastic fabric material shaped to define (1) a main body with top, bottom and opposed side edges, and an inner and an outer surface, and (2) an integral elongated compression strap integral with and extending from said main body approximately midway along one of said side edges such that a portion of said side edge extends above and a portion of said side edge extends below said compression strap;

said side edges being seamed together with said inner surface of said main body facing inwardly and said outer surface facing outwardly, said seam extending at least from approximately said bottom edge of said main body to said elongated compression strap, to thereby define a sleeve portion with a bottom opening and a top opening through which a user's hand extends;

a thumb opening in said sleeve portion;

closure means for bringing said side edges together above said elongated compression strap to thereby close said main body upon itself and define an upper opening in said wrist support through which a user's forearm extends;

said compression strap and said outer surface of said main body including cooperating releasable attachment means, and said strap extending from said main body in a direction such that, and having a sufficient length such that, said compression strap encircles the wrist area at least once in use, whereby after a user's hand and wrist have been inserted into said wrist support, said compression strap can be wrapped snugly around the wrist and releasably fastened to said outer surface of said main body;

said cooperating releasable attachment means associated with said compression strap and said outer surface of said main body facilitate adjustable releasable attachment of said compression strap such that the compression on the user's wrist can be adjusted;

said side edges are also seamed together at a point lying between said compression strap and said closure means.

* * * * *

UNITED STATES PATENT AND TRADEMARK OFFICE
CERTIFICATE OF CORRECTION

PATENT NO. : 5,160,314

DATED : November 3, 1992

INVENTOR(S) : Helena Peters

It is certified that error appears in the above-identified patent and that said Letters Patent is hereby corrected as shown below:

Column 4, line 42:
　　After "core" insert --42 which--.

Column 9, claim 10, line 12:
　　After "body" insert --upon--.

Column 9, claim 13, line 56
　　After "inner" delete --end--.

Signed and Sealed this

Fifteenth Day of February, 1994

Attest:

BRUCE LEHMAN

*Attesting Officer*　　*Commissioner of Patents and Trademarks*